United States Patent
Tsuchiya et al.

(10) Patent No.: US 6,797,656 B2
(45) Date of Patent: Sep. 28, 2004

(54) WATER-ABSORBING COMPOSITES, PREPARATION PROCESSES THEREOF AND WATER-ABSORBING ARTICLES

(75) Inventors: Hiroyoshi Tsuchiya, Yokkaichi (JP); Kouji Katoh, Yokkaichi (JP); Kiichi Itoh, Yokkaichi (JP)

(73) Assignee: Mitsubishi Chemical Corporation, Tokyo (JP)

( * ) Notice: Subject to any disclaimer, the term of this patent is extended or adjusted under 35 U.S.C. 154(b) by 123 days.

(21) Appl. No.: 09/848,439

(22) Filed: May 4, 2001

(65) Prior Publication Data

US 2002/0034911 A1 Mar. 21, 2002

Related U.S. Application Data

(63) Continuation of application No. PCT/JP99/06176, filed on Nov. 6, 1998.

(30) Foreign Application Priority Data

Nov. 6, 1998  (JP) .......................... 10-330283
Feb. 15, 1999  (JP) .......................... 11-035247

(51) Int. Cl.$^7$ .............................. B32B 5/16; B32B 5/26
(52) U.S. Cl. ................. 442/417; 442/381; 442/393; 427/248.1; 427/255.6; 427/180; 427/288; 427/389.9
(58) Field of Search ..................... 442/417, 381, 442/375, 393

(56) References Cited

U.S. PATENT DOCUMENTS

| | | | |
|---|---|---|---|
| 5,180,622 A | | 1/1993 | Berg et al. |
| 5,230,959 A | * | 7/1993 | Young, Sr. et al. ......... 428/372 |
| 5,713,881 A | | 2/1998 | Rezai et al. |
| 5,821,179 A | * | 10/1998 | Masaki et al. .............. 442/375 |
| 5,962,068 A | | 10/1999 | Tsuchiya et al. ............ 427/180 |

FOREIGN PATENT DOCUMENTS

| | | |
|---|---|---|
| JP | 9-67403 | 3/1997 |
| JP | 6-239912 | 9/1997 |
| JP | 10113556 | 5/1998 |
| JP | 11093073 A | 4/1999 |
| JP | WO00/27624 | 5/2000 |

* cited by examiner

Primary Examiner—Cheryl A. Juska
(74) Attorney, Agent, or Firm—Oblon, Spivak, McClelland, Maier & Neustadt, P.C.

(57) ABSTRACT

A water-absorbing composite, containing water-absorbing polymer particles immobilized on a fibrous substrate wherein at least a part of said water-absorbing polymer particles consist of primary particles having an average particle diameter of about 50–1000 μm, wherein about 30% by weight or more of said primary particles are combined to form agglomerates having a shape satisfying the conditions below while nearly maintaining their primary particle shapes and a part of particles of said agglomerates are not adhered to said fibrous substrate. This water-absorbing composite shows excellent water-absorbing properties and a high water-absorbing speed, and most of the highly water-absorbing polymer is stably immobilized on the fibrous substrate and the immobility of swollen gel after absorbing water is also excellent.

Average particle diameter (D) $100 \leq D \leq 3000$ μm
Average relative displacement of the direction by direction analysis (θ) $10 \leq \theta \leq 25$
Frequency analysis 5 Hz/20 Hz intensity ratio (k) $0.6 \leq k \leq 0.9$
Agglomerate maximum length (L)/minimum length (l) ratio $1.2 \leq L/l \leq 15.0$

49 Claims, 4 Drawing Sheets

WATER-ABSORBING COMPOSITES, PREPARATION PROCESSES THEREOF AND WATER-ABSORBING ARTICLES

This application is a continuation of PCT/JP99/06176 filed Nov. 6, 1998.

BACKGROUND OF THE INVENTION

1. Field of the Invention

The present invention relates to water-absorbing composites containing water-absorbing polymer particles in the form of agglomerates immobilized on a fibrous substrate and preparation processes thereof. More specifically, the present invention relates to water-absorbing composites containing agglomerates of water-absorbing polymer particles stably immobilized on a fibrous substrate and having good water-absorbing properties, a high water-absorbing speed and an excellent immobility of swollen gel after absorbing water as well as preparation processes thereof. The present invention also relates to water-absorbing articles using a water-absorbing composite having these characteristics.

2. Description of the Background

Paper, pulp, nonwoven fabric, sponge-like urethane resins or the like have been used as water-retaining materials in various sanitary goods such as sanitary napkins, paper diapers and agricultural materials, for example. However, the water-absorbing capacity of these water-absorbing materials is only 10–50 times their own weight. Thus, larger amounts of materials are required to absorb or retain larger amounts of water, consequently leading to enormous bulk. These materials also have the disadvantage that they readily release water when pressurized after absorbing water.

For the purpose of lessening such disadvantages of these types of materials, various highly water-absorbing polymer materials have recently been proposed, such as starch graft polymers (JP-B 46199/88), modified cellulose (JP-A 80376/75), crosslinked water-soluble polymers (JP-B 23462/68), self-crosslinked acrylic alkali metal salt polymers (JP-B 30710/79), etc.

These water-absorbing polymers exhibit high level of water-absorbing performance, but most are powdery. Accordingly, such water-absorbing polymer powders must be uniformly dispersed on a substrate such as tissue, nonwoven fabric or paper for use as sanitary materials such as sanitary napkins or paper diapers. However, water-absorbing polymer powders dispersed by known methods have the following disadvantages. First, they are difficult to stably immobilize on a fibrous substrate, and even if uniformly dispersed, they often become locally concentrated. Second, swollen gels after absorbing water fail to stably remain on a fibrous substrate but readily move from the fibrous substrate.

When such polymer powders as noted above are uniformly dispersed on a fibrous substrate to give an absorbent, not only are the polymer powders readily separated from the fibrous substrate, but very high cost occurs due to complexity of powder handling and process design for efficient uniform dispersion.

Conventional approaches to addressing these problems include, for example, fixing polymer powder on a fibrous substrate with a binder or coating an aqueous polyacrylic metal salt solution on a substrate and then introducing crosslinkage by a heat-drying process.

However, the former suffers from complexity due to the use of the binder and the latter also has drawbacks, such as insufficient water-absorbing performance.

A process for preparing a water-absorbing composite by preparing a composite containing an aqueous acrylic monomer solution applied in a predetermined pattern on a shaped fibrous substrate and irradiating it with electromagnetic radiations or particulate ionizing radiations to convert the acrylic monomer into a water-swelling polymer has been reported (JP-B 67712/91). This process affords an improved powder handling, such as formation of a uniform dispersion and stable immobilization on a fibrous substrate as described above, but it has the disadvantage that the electromagnetic radiation or particulate ionizing radiation used to convert the acrylic monomer into a water-absorbing polymer markedly accelerates self crosslinking reaction of the water-absorbing polymer to greatly lessen the performance as a water-absorbing material, especially water-absorbing capacity, i.e. usually to half of that obtained with the highly water-absorbing polymer powders previously described. In particular, the highly polymerizable aqueous acrylic monomer solution is absorbed into the fibrous substrate itself to form a very hard plate-like composite after polymerization, which must be broken for actual use. Moreover, absorbing capacity, especially water-absorbing capacity is greatly lowered by the inhibitory effect of the fibrous substrate against swelling of the water-absorbing polymer.

An absorbing article containing a fibrous substrate and a water-absorbing polymer wherein a part of the water-absorbing polymer nearly spherically encloses and discontinuously adheres to the substrate has also been proposed (JP-B 58030/93). This absorbing article affords partially improved water-absorbing characteristics over the above prior products, but it has the disadvantages that hydrophilic fibers are unsuitable for the fibrous substrate though this is a water-absorbing article, and that the water-absorbing polymer loses adhesion and tends to be readily separated after becoming swollen with absorbed water.

Hence, a need exists for a water-absorbing composite which overcomes the above disadvantages.

SUMMARY OF THE INVENTION

Quite surprisingly, it has now been discovered that a water-absorbing composite with excellent water-absorbing properties and water-absorbing speed wherein highly water-absorbing polymer particles are stably immobilized on a fibrous substrate can be prepared by polymerizing droplets of a mixed solution of an aqueous polymerizable acrylic monomer solution initialized with a redox polymerization initiator on a fibrous substrate (JP-A 67403/97).

Accordingly, it is an object of the present invention is to provide a water-absorbing composite with excellent water-absorbing properties and a high water-absorbing speed wherein most of the highly water-absorbing polymer is stably immobilized on a fibrous substrate and the immobility of swollen gel after absorbing water is also excellent and a process for preparing it.

It is also an object of the present invention to provide a water-absorbing article with high practicability using a water-absorbing composite having said properties.

The above objects and others are provided, in part, by a water-absorbing composite, containing water-absorbing polymer particles immobilized on a fibrous substrate wherein at least part of the water-absorbing polymer particles contain primary particles having an average particle diameter of about 50–1,000 $\mu$m, wherein about 30% by weight or more of the primary particles are considered to form agglomerates having a shape satisfying the following conditions while nearly maintaining their primary particle shapes and a part of particles of the agglomerates are not adhered to the fibrous substrate:

Average particle diameter (D) $100 \leq D \leq 3000$ μm

Average relative displacement of the direction by direction analysis (θ) $10 \leq \theta \leq 25$ Frequency analysis 5 Hz/20 Hz intensity ratio (k) $0.6 \leq k \leq 0.9$ Agglomerate maximum length (L)/minimum length (l) ratio $1.2 \leq L/l \leq 15.0$.

DETAILED DESCRIPTION OF THE PREFERRED EMBODIMENTS

Figure 1:
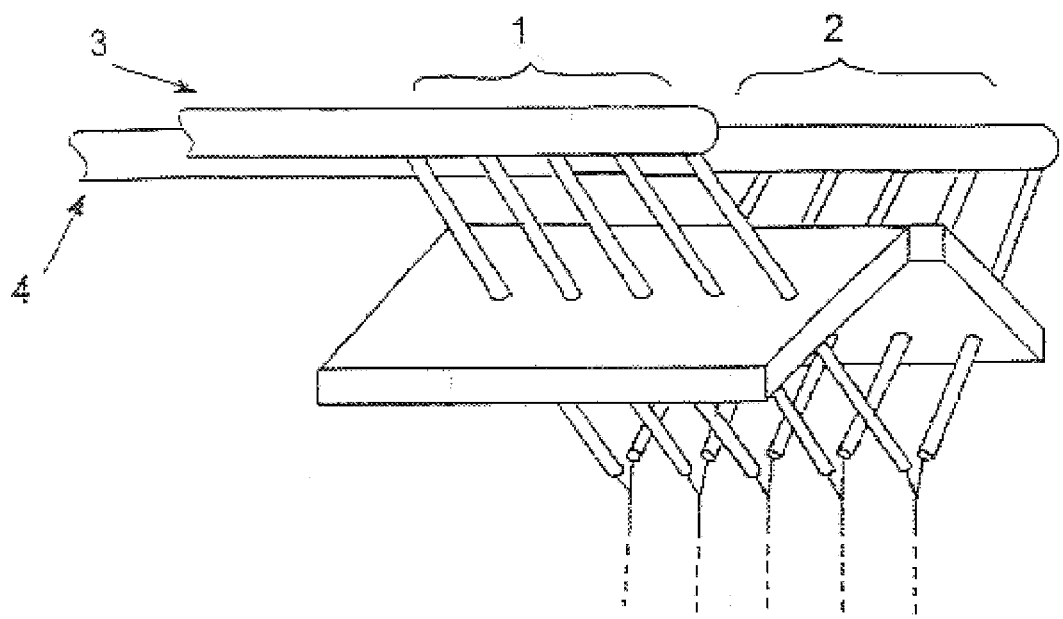
FIG. 1 is a schematic view showing an example of the nozzle structure used to carry out the mixing step in a process of the present invention, in which numeral references represent the following elements. 1: nozzles for a first solution, 2: nozzles for a second solution, 3: solution A, 4: solution B.

The present invention provides a water-absorbing composite containing water-absorbing polymer particles immobilized on a fibrous substrate wherein at least a part of the water-absorbing polymer particles contain primary particles having an average particle diameter of about 50–1000 μm, 30% by weight or more of the primary particles being combined to form agglomerates having a shape satisfying the conditions below while nearly maintaining their primary particle shapes and a part of particles of said agglomerates are not adhered to said fibrous substrate:

Average particle diameter (D) $100 \leq D \leq 3000$ μm

Average particle displacement of the direction by direction analysis (θ) $10 \leq \theta \leq 25$ Frequency analysis 5 Hz/20 Hz intensity ratio (k) $0.6 \leq k \leq 0.9$ Agglomerate maximum length (L)/minimum length (l) ratio $1.2 \leq L/l \leq 15.0$.

The present invention also provides a process for preparing a water-absorbing composite, containing forming droplets of a reaction mixture initialized by mixing an aqueous solution of a polymerizable monomer giving a water-absorbing polymer with a redox polymerization initiator in a gas phase, combining said droplets into agglomerates while nearly maintaining their primary particle shapes in the gas phase and/or on a fibrous substrate, supporting said agglomerates formed in the gas phase on said fibrous substrate, and then completing polymerization of said agglomerates on said fibrous substrate to immobilize said agglomerates on said fibrous substrate.

The present invention also provides a water-absorbing article containing a water-absorbing material having water-absorbing polymer particles immobilized on one side of a fibrous substrate so that said water-absorbing polymer particles absorb aqueous liquids through said fibrous substrate, wherein at least a part of said water-absorbing polymer particles contain primary particles having an average particle diameter of about 50–1000 μm, 30% by weight or more of said primary particles are combined to form agglomerates having a shape satisfying the conditions below while nearly maintaining their primary particle shapes and a part of particles of said agglomerates are not adhered to said fibrous substrate:

Average particle diameter (D) $100 \leq D \leq 3000$ μm

Average relative displacement of the direction by direction analysis (θ) $10 \leq \theta \leq 25$ Frequency analysis 5 Hz/20 Hz intensity ratio (k) $0.6 \leq k \leq 0.9$ Agglomerate maximum length (L)/minimum length (l) ratio $1.2 \leq L/l \leq 15.0$.

The present invention also provides a water-absorbing article containing a water-absorbing material having water-absorbing polymer particles immobilized on one side of a fibrous substrate so that said water-absorbing polymer particles absorb aqueous liquids through said fibrous substrate, wherein immobilization of said water-absorbing polymer particles is carried out by forming droplets of a reaction mixture initialized by mixing an aqueous solution of a polymerizable monomer giving a water-absorbing polymer with a redox polymerization initiator in a gas phase, combining said droplets into agglomerates while nearly maintaining their primary particle shapes in the gas phase and/or on a fibrous substrate, supporting said agglomerates formed in the gas phase on said fibrous substrate, and then completing polymerization of said agglomerates on said fibrous substrate to immobilize said agglomerates on said fibrous substrate.

Water-absorbing composites, processes for preparing water-absorbing composites and water-absorbing articles of the present invention are explained below in detail with reference to preferred embodiments, which are provided solely for purposes of illustration and are not intended to be limitative.

Water-absorbing Composites

Water-absorbing composites of the present invention comprise water-absorbing polymer particles immobilized on a fibrous substrate (hereinafter also simply referred to as "substrate"). A part of water-absorbing polymer particles contain primary particles having an average particle diameter of about 50–1000 μm, preferably about 100–900 μm, more preferably about 200–800 μm. As used herein throughout, the symbol "-" means a range defined by the recited figures both inclusive as a minimum and a maximum.

Thirty % by weight or more, preferably about 50% or more, more preferably about 80% or more of primary particles are combined to form agglomerates while maintaining their primary particle shapes. A part of particles forming agglomerates are not adhered to the fibrous substrate. That is, agglomerates consist of primary particles directly adhered to the fibrous substrate and primary particles not adhered to the fibrous substrate. Such agglomerates have a high water-absorbing speed because of the large specific surface area, while they have an excellent water-absorbing capacity because only a part of primary particles forming agglomerates are adhered to the fibrous substrate so that the fibrous substrate imposes less constraints on swelling with absorbed water. Moreover, agglomerates are scarcely broken into primary particles and separated from the fibrous substrate before and even after absorbing water because joint surfaces of primary particles forming agglomerates are fused together.

Agglomerates are characterized by a specific range of average particle diameter (D), average relative displacement of the direction by direction analysis (θ), frequency analysis 5 Hz/20 Hz intensity ratio (k) and agglomerate maximum length (L)/minimum length (l) ratio as defined above. Agglomerates have an average particle diameter (D) of about 100–3000 μm, preferably about 200–2000 μm, more preferably about 250–2000 μm. If the average particle diameter is smaller than 100 μm, water-absorbing performance is not sufficiently shown. If the average particle diameter is greater than 3000 μm, adhesion to the fibrous substrate decreases.

Average relative displacement of the direction by direction analysis (θ) is about 10–25, preferably about 12–24, more preferably about 14–22. Frequency analysis 5 Hz/20 Hz intensity ratio (k) is about 0.6–0.9, preferably about 0.65–0.85, more preferably about 0.65–0.80. Agglomerate maximum length (L)/minimum length (l) ratio is about 1.2–15.0, preferably about 1.5–10.0, more preferably about 1.5–8.0. These average particle diameter (D), average relative displacement of the direction by direction analysis (θ), frequency analysis 5 Hz/20 Hz intensity ratio (k) and agglomerate maximum length (L)/minimum length (l) ratio can be determined by the methods described later in test examples.

Water-absorbing composites of the present invention are characterized by their ability to maintain a soft touch because primary polymer particles in the form of a true sphere are combined together with secondary particles which are unangular in the form of grapes. A water-absorbing composite containing a water-absorbing polymer immobilized on a fibrous substrate similarly to the present invention has been developed and disclosed in JP-A 67403/97, but the water-absorbing resin in the composite described therein consists of angular and irregular single particles adhered to fibers so that skin touch is rough or prickly but not soft. On the contrary, the water-absorbing composites of the present invention provide a greatly improved skin touch sensation.

Water-absorbing polymer particles are contained in water-absorbing composites normally in an amount of about 50–300 g/m², preferably about 100–250 g/m², especially about 130–220 g/m². If the content of water-absorbing polymer particles is low, water-absorbing capacity is, of course, low. Excessive contents are uneconomic and decrease the proportion of primary particles adhered to the fibrous substrate to lower adhesion to the substrate.

Processes for preparing water-absorbing composites of the present invention are not specifically limited. Water-absorbing composites prepared by any processes are included in the scope of the present invention so far as they satisfy the claimed conditions. Materials of water-absorbing polymer particles and fibrous substrates forming water-absorbing composites of the present invention are not specifically limited, either. Therefore, known water-absorbing polymers and fibrous substrates can be used. A plurality of materials can be used in combination. Specific examples of water-absorbing polymers and fibrous substrates will be described later. In water-absorbing composites of the present invention, water-absorbing polymers may be immobilized on either only one side or both sides of a fibrous substrate, depending on the purpose of the water-absorbing composites. For example, water-absorbing polymers can be immobilized on both sides of a fibrous substrate to increase the basic weight on the fibrous substrate or share functions between both sides.

Processes for Preparing Water-absorbing Composites

Water-absorbing composites suitable for the purpose of the present invention can be simply and economically prepared by processes of the present invention. Processes of the present invention comprise forming droplets of a reaction mixture initialized by mixing an aqueous solution of a polymerizable monomer giving a water-absorbing polymer with a redox polymerization initiator in a gas phase, combining said droplets into agglomerates while nearly maintaining their primary particle shapes in the gas phase and/or on a fibrous substrate, supporting said agglomerates formed in the gas phase on said fibrous substrate, and then completing polymerization of said agglomerates on said fibrous substrate to immobilize said agglomerates on said fibrous substrate.

Polymerizable Monomers

Polymerizable monomers used in the present invention may be of any type so far as they give a water-absorbing polymer and are initialized with a redox polymerization initiator. These monomers must be water-soluble because they are used as aqueous solutions, though monomers giving a water-absorbing polymer are normally water-soluble.

Typical examples of these monomers preferably suitable for use in the present invention are aliphatic unsaturated carboxylic acids or salts thereof, specifically unsaturated monocarboxylic acids or salts thereof such as acrylic acid or salts thereof, methacrylic acid or salts thereof, or unsaturated dicarboxylic acids or salts thereof such as maleic acid or salts thereof, itaconic acid or salts thereof, which may be used alone or in combination.

Among these, acrylic acid or salts thereof and methacrylic acid or salts thereof are preferred, with especially preferred being acrylic acid or salts thereof.

Polymerizable monomers giving a water-absorbing polymer in the present invention are preferably aliphatic unsaturated carboxylic acids or salts thereof as described above, therefore, aqueous solutions of these polymerizable monomers are preferably aqueous solutions essentially containing an aliphatic unsaturated carboxylic acid or a salt thereof. As used herein, the expression "essentially containing an aliphatic unsaturated carboxylic acid or a salt thereof" means that the aliphatic unsaturated carboxylic acid or a salt thereof is contained at 50 mol % or more, preferably 80 mol % or more on the basis of the total amount of the polymerizable monomer.

Suitable salts of aliphatic unsaturated carboxylic acids normally include water-soluble salts such as alkali metal salts, alkali earth metal salts, ammonium salts or the like. The neutrality is appropriately selected depending on the purpose, but 20–90 mol % of carboxyl group is preferably neutralized with an alkali metal salt or an ammonium salt in the case of acrylic acid. If the partial neutrality of an acrylic monomer is less than 20 mol %, the resulting water-absorbing polymer tends to have much low water-absorbing capacity.

Acrylic monomers can be neutralized with alkali metal hydroxides or bicarbonates or ammonium hydroxide or the like, preferably alkali metal hydroxides such as sodium hydroxide and potassium hydroxide.

In addition to said aliphatic unsaturated carboxylic acids, monomers copolymerizable with them such as (meth)acrylamide, (poly)ethylene glycol (meth)acrylate, 2-hydroxyethyl (meth)acrylate or even slightly water-soluble monomers including acrylic alkyl esters such as methyl acrylate or ethyl acrylate may also be copolymerized in an amount within a range that does not affect performance of the resulting water-absorbing polymers in the present invention. As used herein, the term "(meth)acryl" means both "acryl" and "methacryl".

Among these polymerizable monomers, those giving a water-absorbing polymer may also be used as main monomers of "an aqueous solution of a polymerizable monomer giving a water-soluble polymer" rather than auxiliary components to aliphatic unsaturated carboxylic acids or salts thereof.

Aliphatic unsaturated carboxylic acids or salts thereof, especially acrylic acid or salts thereof sometimes form a self-crosslinked polymer by themselves, but may be positively induced to form a crosslinked structure using a crosslinker. The use of a crosslinker normally improves water-absorbing performance of the resulting water-absorbing polymer. Preferably, suitable crosslinkers include divinyl compounds copolymerizable with said polymerizable monomers such as N,N'-methylenebis(meth)acrylamide, (poly)ethylene glycol (meth)acrylate and water-soluble compounds having two or more functional groups capable of reacting with a carboxylic acid including polyglycidyl ethers such as ethylene glycol diglycidyl ether, polyethylene glycol diglycidyl ether. Among them, N,N'-methylenebis(meth)acrylamide is especially preferred. Crosslinkers are used in an amount of 0.001–1% by weight, preferably 0.01–0.5% by weight on the basis of the amount of the monomer.

The concentration of polymerizable monomers in an aqueous polymerizable monomer solution essentially containing an aliphatic unsaturated carboxylic acid or a salt thereof as described above is 20% or more, preferably 25% or more. Concentrations less than 20% by weight are not preferred because droplets having an appropriate viscosity are difficult to produce whereby the resulting water-absorbing polymer has insufficient water-absorbing capacity. The upper limit is preferably about 80% by weight in respect of handling of the polymerization reaction solution.

Redox Polymerization Initiators

Polymerization initiators used in the present invention should be somewhat water-soluble redox systems combining an oxidizing radical generator and a reducing agent. Such oxidizing agents include hydrogen peroxide, persulfates such as ammonium persulfate or potassium persulfate, peroxides including hydroperoxides such as t-butyl hydroperoxide or cumene hydroperoxide, secondary cerium salts, permanganates, chlorites, hypochlorites, etc., among which hydrogen peroxide is especially preferred. These oxidizing agents are used in an amount of about 0.01–10% by weight, preferably about 0.1–2% by weight on the basis of polymerizable monomers.

Suitable reducing agents are capable of forming a redox system with said oxidizing agents, specifically sulfites such as sodium sulfite or sodium hydrogensulfite, sodium thiosulfate, cobalt acetate, copper sulfate, ferrous sulfate, L-ascorbic acid or L-ascorbic acid alkali metal salts, etc. Among others, L-ascorbic acid or L-ascorbic acid alkali metal salts are especially preferred. These reducing agents are used in an amount of about 0.001–10% by weight, preferably about 0.01–2% by weight on the basis of polymerizable monomers.

Polymerization Processes

In the present invention, an aqueous solution of a polymerizable monomer giving a water-absorbing polymer, specifically an aqueous solution of a polymerizable monomer essentially containing an aliphatic unsaturated carboxylic acid or a salt thereof is initialized with a redox polymerization initiator and, after initiation of the reaction, the reaction mixture under polymerization containing the monomer and the produced polymer is divided into droplets in a gas phase and the droplets are combined into agglomerates in the gas phase and/or on a fibrous substrate, and then polymerization of the agglomerates is completed on the fibrous substrate. Thus, polymerization is completed after the agglomerates are supported on said fibrous substrate (optionally supporting the agglomerates) if they are formed in a gas phase or directly completed if they are formed on the fibrous substrate. As used herein, the expression "on a fibrous substrate" includes on the face of a shaped fibrous substrate, on fibers of the substrate and on the inner faces of spaces between fibers of the substrate.

In this polymerization format, it is necessary to select operating conditions which allow the initiated monomer-containing aqueous solution to form droplets having a determined viscosity to produce agglomerates and firmly adhere them to the substrate, taking into much account that polymerization is initialized substantially as soon as a redox system is formed in the presence of the monomer and that the polymerization initiated with the redox polymerization initiator is a chain polymerization, and correspondingly that the time to reach a desired polymerization degree or the time for the monomer-containing aqueous solution to reach a desired level of viscosity is relatively short.

Under these considerations, a preferred method comprises initiating polymerization by mixing a first solution consisting of an aqueous polymerizable monomer solution containing either one of an oxidizing agent or a reducing agent forming a redox polymerization initiator and a second solution consisting of an aqueous solution containing the other component of the redox polymerization initiator and optionally the polymerizable monomer in a gas phase.

Specifically, the first and second solutions are discharged from separate nozzles in such a manner that they collide with each other in a liquid column state at a crossing angle of about 15° or more. Thus, both solutions are collided at some crossing angle so that a part of the energy produced by discharging from nozzles is used for mixing. The crossing angle between the first and second solutions discharged from the respective nozzles is appropriately chosen depending on the properties of the polymerizable monomer used, the flow rate ratio or other factors. For example, the crossing angle may be small if the linear velocity of the solutions is high. The angle should be about 15 or more, preferably about 20 or more for attaining sufficient mixing effect. The upper limit of the angle is not specifically limited so far as a liquid column is formed after the first and second solutions collide with each other (as detailed later), but the maximum angle is about 120 or less, preferably about 100 or less for industrial apparatus.

In this method, the first and second solutions exiting the respective nozzles must be collided in a liquid column state so that both solutions combine to form a liquid column. The solutions thus collided in a liquid state can be mixed in a selected flow rate ratio to achieve a good polymerization reaction. If the first and second solutions are collided after they have formed particles, favorable results are hardly obtained because the mixing ratio shifts from the selected flow rate ratio. The distance between nozzle tips can be freely determined within the range that allows fluids to be collided in a liquid column state, and nozzle tips may be in contact with each other. Nozzles may have an inner diameter appropriately chosen depending on the properties of the polymerizable monomer used and the shape of the intended water-absorbing composite, preferably in the range of about 0.15–2.0 mm, more preferably about 0.1–1.0 mm.

In this case, the temperature of the first solution is normally ordinary temperatures to about 60° C., preferably ordinary temperatures to about 40° C., and the temperature of the second solution is also normally ordinary temperatures to about 60° C., preferably ordinary temperatures to about 40° C.

Thus, the aqueous solutions discharged from the respective nozzles are collided in a liquid column state to combine into one stream. The combined solutions form a liquid column and maintain this state for a period, and then this liquid column is broken into droplets. The resulting droplets fall in a gas phase or on a substrate to form agglomerates there.

The period for which the combined solutions form and maintain a liquid column, the height of the liquid column and the sizes of droplets depend on selected conditions such as the inner diameters of nozzles, but normally said period is about 0.1–3 seconds, the height of the liquid column is about 3–50 mm, and the sizes of droplets are about 5–3000 $\mu$m in diameter. Especially, the sizes of droplets are preferably in a range of about 50–1000 $\mu$m in order that polymerization of droplets proceeds to combine them into appropriate agglomerates.

The gas phase providing a place in which polymerization is initiated and droplets are formed during polymerization is preferably a gas inert to the polymerization such as nitrogen, helium, carbon dioxide, but may also be air. The humidity in the gas is not specifically limited and the gas may wholly consist of water vapor, but if the humidity is too low, moisture in the aqueous monomer solution evaporates to precipitate the monomer before polymerization proceeds, with the result that polymerization speed may be much lowered or polymerization may stop halfway. The temperature condition of the gas is room temperature or more but about 150° C. or less, preferably about 100° C. or less. The direction of gas flow may be either parallel or counter to the travel direction of the liquid column and droplets, but counter flow (counter-gravity direction) is preferred when droplets are required to stay longer in a gas phase or when the polymerization degree of the polymerizable monomer, and therefore the viscosity of droplets should be increased.

Fibers forming the substrate are preferably hydrophilic fibers such as wood pulp, rayon, cotton, regenerated cellulose or other cellulose fibers because they are used in water-absorbing articles, and these fibers derive the greatest benefit from the present invention and substrates based on such a hydrophilic fiber are especially preferred in the present invention. Other suitable fibrous substrates are based on polyester fibers or other classes of non-hydrophilic fibers such as polyethylene, polypropylene, polystyrene, polyamide, polyvinyl alcohol, polyvinyl chloride, polyvinylidene chloride, polyacrylonitrile, polyurea, polyurethane, polyfluoroethylene, polyvinylidene cyanide fibers. Relatively dense fibrous substrates made of paper, wood, back skin, leather or the like may also be used.

Various conditions should be selected so that the polymerization degree may be about 20–97%, preferably about 30–97%, more preferably about 50–95% when droplets under polymerization form agglomerates in a gas phase or on a substrate. If the polymerization degree is too low, droplets cannot be adhered in the form of agglomerates to the substrate because even droplets colliding with each other in a gas phase combine into gross particles without forming agglomerates or droplets falling on the substrate spread or are absorbed or impregnated into the substrate. If the polymerization degree is too high, adhesion to the substrate is not ensured and adhesion between the substrate and the water-absorbing polymer is affected.

The polymerization degree and agglomeration can be controlled by modulating the crossing angle between the first and second solutions discharged from nozzles, the diameters of nozzles, the nature and amount of the polymerization initiator, the distance between nozzles and the substrate, the temperature and humidity of the gas phase, the number and configuration of nozzles, and the relative position or distance between nozzles and the substrate to increase the probability of collision between solutions or adjust the polymerization level in the gas phase. Other methods than using two opposed nozzles may also be used, such as, for example, a bundle type nozzle sprayer having two nozzles with aligned tips, or a double nozzle sprayer in which one nozzle is inserted into the other nozzle.

Components of solutions discharged from the respective nozzles collide and mix with each other in a liquid column state and then form droplets, which are polymerized into agglomerates during or after falling on a substrate, whereby a final polymerization stage proceeds on the substrate.

If desired, unreacted monomers remaining in agglomerates may be treated to react them, by means of 1) promoting polymerization of the monomers, 2) directing the monomers into other derivatives, or 3) removing the monomers.

Means of 1) promoting polymerization of the monomers include, for example, further heating the composite of agglomerates and a substrate, or adding a catalyst or a catalytic element which promotes polymerization of the monomers to agglomerates and then heating them, or irradiating the composite with UV rays, electromagnetic radiations or particulate ionizing radiations, etc.

The method of further heating the composite of agglomerates and a substrate involves heating the composite of agglomerates and a substrate at about 100–250° C. to polymerize monomers remaining in the agglomerates.

The method of adding a catalyst or a catalytic element which promotes polymerization of the monomers to agglomerates involves adding a solution of a reducing agent to agglomerates when a redox polymerization initiator is used for polymerization, for example, because the radical generator frequently remain. Suitable reducing agents are sodium sulfite, sodium hydrogensulfite, L-ascorbic acid or the like used as redox polymerization initiators, and they may be normally added as aqueous 0.5–5% by weight solutions to agglomerates. Reducing agents may be added in an amount of 0.1–2% by weight on the basis of dry resin. Reducing agents may be added by any method such as spraying with an atomizer or immersing into a reducing agent in solution. After a reducing agent is added, agglomerates are then heated to polymerize polymerizable monomers. Heating may be carried out at 100–150° C. for about 10–30 minutes, for example. This heating lowers the moisture content of agglomerates, but if the moisture content is still high, the agglomerates are further dried in a dryer to give a product water-absorbing composite.

The method of irradiating a composite of agglomerates and a substrate with UV rays involves using ordinary UV lamps. The irradiation intensity, irradiation period or other conditions depend on the nature of the fibrous substrate, the impregnation level of the remaining monomers or other factors, but irradiation normally takes place with UV lamps at about 10–200 W/cm, preferably about 30–120 W/cm for an irradiation period of about 0.1 second-30 minutes at a lamp-composite distance of 2–30 cm. The moisture content of the composite here is normally about 0.01–40 parts by weight, preferably about 0.1–1.0 parts by weight per 1 part by weight of the polymer. Moisture contents less than 0.01 parts by weight or more than 40 parts by weight are not preferred because they greatly affect reduction of remaining monomers. UV irradiation may be performed in a vacuum, or in the presence of an inorganic gas such as nitrogen, argon or helium, or in the air. The irradiation temperature is not specifically limited, and the intended purpose can be sufficiently achieved at room temperature. The UV irradiation apparatus used is not specifically limited, either, but any method can be applied such as stationary irradiation for a determined period or continuous irradiation on a belt conveyor.

The method of irradiating a composite of agglomerates and a substrate with radiations involves using high-energy radiations such as accelerated electrons or gamma rays.

The dose to be applied depends on the amount of remaining monomers in the composite, the moisture content or the like, but normally ranges from about 0.01 to 100 Mrad, preferably about 0.1 to 50 Mrad. If the dose exceeds 100 Mrad, water-absorbing capacity is much low. If the dose is less than 0.01 Mrad, it is difficult to obtain a desired composite having high water-absorbing capacity or water-absorbing speed and much reduced remaining monomers. The moisture content in the composite here is normally 40 parts by weight or less, preferably 10 parts by weight or less per 1 part by weight of the fibrous substrate. Moisture contents in excess of 40 parts by weight are not preferred because water-absorbing speed is less improved and especially, reduction of remaining monomers is greatly affected. According to the present invention, the composite may be irradiated with a high-energy radiation in a vacuum, or in the presence of an inorganic gas such as nitrogen, argon or helium, or in the air. A preferred atmosphere is the air, and if irradiation is performed in the air, water-absorbing capacity or water-absorbing speed is increased and remaining monomers are remarkably reduced. The irradiation temperature is not specifically limited, and the intended purpose can be sufficiently achieved at room temperature.

Means of 2) directing the monomers into other derivatives include, for example, adding an amine, ammonia or the like or a reducing agent such as hydrogensulfites, sulfites, pyrosulfites or the like.

Means of 3) removing the monomers include, for example, extraction with an organic solvent or distillation. Extraction with an organic solvent involves immersing a composite of agglomerates and a substrate into an aqueous organic solvent to extract off the remaining monomers. Suitable aqueous organic solvents include ethanol, methanol, acetone or the like preferably having a moisture content of about 10–99% by weight, especially about 30–60% by weight. Generally, the higher the moisture content, the higher the ability of removing remaining monomers, but energy consumption increases during the subsequent drying step if aqueous organic solvents having a high moisture content are used. The period for which the composite of agglomerates and a substrate is immersed in an aqueous organic solvent may be normally about 5–30 minutes, and it is also preferable to use a means of promoting extraction of remaining monomers such as rocking the composite of agglomerates and a substrate. After immersion, the composite may be dried in a dryer.

Distillation of the monomers involves treating the composite of agglomerates and a substrate with overheated water vapor or a water vapor-containing gas. For example, saturated water vapor of 110° C. can be heated to about 120–150° C. and brought into contact with a composite of agglomerates and a substrate as overheated water vapor to reduce the remaining monomers in the agglomerates. According to this method, it is thought that the remaining monomers can also be vaporized off from the agglomerates when water in the agglomerates evaporates as water vapor. This method combines the step of removing the remaining monomers with the step of drying the product.

For the purpose of improving water-absorbing performance, the surfaces of agglomerates on the substrate can be crosslinked with a crosslinker. Generally, it is known to improve characteristics of resin particles by adding a crosslinker on the surfaces of powdery water-absorbing resin particles and then crosslinking the surfaces by heating, and it is thought that these particles can maintain their shapes without receiving inhibition against swelling with water absorbed because crosslinked structures are selectively formed on the surfaces. This process begins with adding a surface crosslinker in solution to agglomerates of a composite of agglomerates and a substrate. Suitable surface crosslinkers are polyfunctional compounds copolymerizable with polymerizable monomers such as N,N'-methylenebis(meth)acrylamide or (poly)ethylene glycol bis (meth)acrylate, or compounds having a plurality of functional groups capable of reacting with carboxylate group such as (poly)ethylene glycol diglycidyl ether. These surface crosslinkers are normally used in an amount of about 0.1–1% by weight, preferably about 0.2–0.5% by weight on the basis of agglomerates (dry basis). These surface crosslinkers are preferably used as solutions diluted at about 0.1–1% by weight, especially about 0.2–0.5% by weight in water, ethanol, or methanol, for example, so that they may be uniformly dispensed on the entire surfaces of agglomerates. Preferably, crosslinkers in solution are dispensed normally by using an atomizer to spray a crosslinker solution on agglomerates, or using a roll brush immersed at the base in a tank containing a crosslinker solution to apply the crosslinker solution on a composite of agglomerates and a substrate while it is being moved with the side to be coated with resin particles facing downward. After a crosslinker solution is excessively applied, an excess of the crosslinker solution may be removed by air blasting or mildly pressing the composite between pressure rolls without crushing resin particles. These crosslinker solutions may be applied at room temperature. After a crosslinker solution is added, the composite of agglomerates and a substrate is then heated to promote crosslinking reaction to selectively form crosslinked structures on the surfaces of agglomerates. Conditions for the for crosslinking reaction may be appropriately selected depending on the crosslinker used, but the reaction is normally performed at a temperature of 100° C. or more for 10 minutes or more.

Water-absorbing composites prepared by a process of the present invention have excellent water-absorbing properties and a high water-absorbing speed, and most of the highly water-absorbing polymer is stably immobilized on the fibrous substrate, and the immobility of swollen gel after absorbing water is also excellent. A prior art related to the present invention, JP-A 239912/97, discloses a process for preparing a water-absorbing composite comprising providing water-absorbing polymer particles immersed with a water-soluble ethylenically unsaturated monomer on a fibrous substrate or a substrate and then polymerizing the ethylenically unsaturated monomer in said water-absorbing polymer particles to immobilize the water-absorbing polymer particles on said fibrous substrate or said substrate. In this process, fibers in the fibrous substrate are point-bonded to the surfaces of primary particles of agglomerates because the water-absorbing resin polymer particles used have been completely polymerized. On the contrary, the present invention intends to bond incompletely polymerized particles to fibers in the fibrous substrate so that the fibers in the fibrous substrate penetrate into a part of primary particles of agglomerates. As compared with JP-A 239912/97, water-absorbing resins of water-absorbing composites of the present invention have remarkably improved bonding strength during water absorption as evident from the bonding mechanism.

Fibrous Substrates

The fibrous substrate to which said droplets or agglomerates of the reaction mixture under polymerization are to be adhered is preferably a shaped fibrous substrate. As used herein, the shaped fibrous substrate specifically means a woven or nonwoven or knitted fabric consisting of loosely shaped fibers in a specific form such as a pad, carded or air-laid web, tissue paper, cotton gauze, etc., which may require cutting, joining, shaping or other processes but no more web-forming process to incorporate the fibrous substrate into an article.

Fibers forming the substrate are preferably hydrophilic fibers such as wood pulp, rayon, cotton, regenerated cellulose or other cellulose fibers because they are used in water-absorbing articles, and these fibers derive the greatest benefit from the present invention and substrates based on such a hydrophilic fiber are especially preferred in the present invention. Other suitable fibrous substrates are based on polyester fibers or other classes of non-hydrophilic fibers such as polyethylene, polypropylene, polystyrene, polyamide, polyvinyl alcohol, polyvinyl chloride, polyvinylidene chloride, polyacrilonitrile, polyurea, polyurethane, polyfluoroethylene, polyvinylidene cyanide fibers. Relatively dense fibrous substrates made of paper, wood, back skin, leather or the like may also be used.

Preparation of Water-absorbing Composites

A process for practically preparing a water-absorbing composite is illustrated as follows. A liquid column of a reaction mixture under polymerization initiated with an aqueous polymerizable monomer solution is fallen on a sheet of said fibrous substrate which is being moved on a belt conveyor, and the resulting droplets are combined in a gas phase or on the fibrous substrate sheet to form agglomerates, which are then supported on said substrate sheet for a period to complete polymerization. The resulting water-absorbing polymer containing moisture is dried to remove the moisture, whereby a web of water-absorbing composite is obtained. This is cut into desired shape and size to give a water-absorbing composite product.

Water-absorbing Composite

Thus obtained water-absorbing composite comprises a water-absorbing polymer in the form of agglomerates supported on a fibrous substrate in such a manner that at least a part of the agglomerates are immobilized on the fibrous substrate to surround or touch fibers of the substrate and the fibers penetrate into a part of primary particles. Therefore, said polymer is firmly immobilized on the fibrous substrate not only before water is absorbed but also after it is gelled with water absorbed. Moreover, joint surfaces of primary particles forming agglomerates are fused together without any bonding interface so that agglomerates are excellent in keeping their shapes as absorbing materials less liable to return to single particles even after they are swollen with water absorbed. Such a water-absorbing polymer of the present invention is characterized by the low possibility of separation after absorbing water, as evident from the supporting rate representing the supporting strength of the water-absorbing polymer on a fibrous substrate described later.

Water-absorbing composites of the present invention are also characterized by excellent water-absorbing capacity because the water-absorbing polymer is in the form of agglomerates and a part of primary particles forming the agglomerates are not adhered to fibers of the substrate, whereby said polymer is less constrained by substrate fibers and less hindered by the fibers from being swollen with water absorbed.

Water-absorbing composites of the present invention also have satisfactory performance in water-absorbing capacity and water-absorbing speed as evident from physiological saline-absorbing capacity and absorbing speed tests described in the examples (and comparative examples) later. According to the present invention, water-absorbing capacity is typically 20 (times) or more, normally 30 (times) or more, often 35 (times) or more. Water-absorbing speed is typically 15 g/5 min or more, normally 20 g/5 min or more, often 25 g/5 min or more.

Water-absorbing composites of the present invention are also satisfactory in respect of their low residual unreacted monomer level. According to the present invention, the residual unreacted monomer level is typically 500 ppm or less, normally 300 ppm or less, often 100 ppm or less.

Water-absorbing composites of the present invention can be used for the same purposes as those of conventional water-absorbing resins. They can be appropriately used for various purposes of water-absorbing resins as introduced in "Water-absorbing Polymers", pp. 81–111 (Masuda, Kyoritsu Shuppan, 1987); "Trend of development and applications of highly water-absorbing resins" (Omori, Technoforum, 1987); Tanaka in "Industrial materials", Vol. 42, No. 4, pp. 18–26, 1994; and Harada et al. ditto, pp. 26–30; such as paper diapers, sanitary goods, freshness-keeping materials, moisture-retaining materials, low-temperature insulating materials, anti-sweating materials, soil-improving materials, etc.

They can also be used for the purposes of sheet-like water-absorbing composites as proposed in JP-A 267370/88, 10667/88, 295251/88, 270801/88, 294716/88, 64602/89, 231940/89, 243927/89, 30522/90, 153731/90, 21385/91, 133728/92, or 156118/99, for example.

Water-absorbing Articles

Water-absorbing articles of the present invention comprise a water-absorbing material having water-absorbing polymer particles immobilized on one side of a fibrous substrate (hereinafter sometimes simply referred to as "water-absorbing material") so that said water-absorbing polymer particles absorb aqueous liquids through said fibrous substrate, characterized in that a water-absorbing composite of the present invention described above or a water-absorbing composite prepared by a process of the present invention described above is used. Among water-absorbing composites, those having water-absorbing polymer particles immobilized on one side of a fibrous substrate are herein specifically called water-absorbing materials.

Water-absorbing articles of the present invention essentially comprise a fibrous substrate and a water-absorbing polymer, i.e. a water-absorbing material having a water-absorbing polymer immobilized on only one side of a fibrous substrate, appropriately combined with materials commonly used in water-absorbing articles such as fluffy pulp, paper, nonwoven fabric, polyolefin films, etc. The water-absorbing material here is arranged in such a manner that a water-absorbing face is provided on the fibrous substrate side. Thus, aqueous liquids to be absorbed pass through the fibrous substrate of the water-absorbing material to reach water-absorbing polymer particles. This ensures that a water-absorbing article which allows rapid absorption and hardly releases the absorbed aqueous liquids even under pressure can be obtained.

Similarly to water-absorbing articles, especially so-called paper diapers or sanitary napkins using a bulking material such as fluffy pulp to improve body fit during use, water-absorbing articles of the present invention preferably have a layer of a bulking material such as fluffy pulp. The fluffy pulp layer is preferably provided on the water-absorbing polymer side at a basic weight of 80–250 g/m$^2$, especially 100–220 g/m$^2$. When a fluffy pulp layer is provided on each side of a water-absorbing material, the basic weight is preferably higher on the water-absorbing polymer side than the fibrous substrate side. If a fluffy pulp layer having a higher basic weight is provided on the fibrous substrate side, aqueous liquids to be absorbed are absorbed more slowly to the main absorbent water-absorbing material because they pass through the hydrophilic fluffy pulp layer to reach the water-absorbing material. Contrary to the water absorbed in water-absorbing polymer particles, the water absorbed in fluffy pulp is readily released so that it is readily removed when the water-absorbing article is pressed after absorbing water.

Additives

Water-absorbing polymers, water-absorbing composites or water-absorbing articles may contain various additives to provide a desired function depending on the intended purpose. These additives include stabilizers for preventing polymer decomposition or denaturation by liquids absorbed, antibacterial agents, deodorants, deodorizers, fragrances, foaming agents, etc.

Stabilizers for preventing polymer decomposition or denaturation by liquids absorbed include stabilizers for preventing decomposition or denaturation of water-absorbing resins by excreta (i.e. human urine or feces) or biological liquids (such as human blood, menstrual blood, secreted liquids). JP-A 118375/88 proposes a method for incorporating an oxygen-containing reducing inorganic salt and/or an organic antioxidant into a polymer; JP-A 153060/88 proposes a method for incorporating an oxidizing agent; JP-A 127754/88 proposes a method for incorporating an antioxidant; JP-A 272349/88 proposes a method for incorporating a sulfur-containing reducing agent; JP-A 146964/88 proposes a method for incorporating a metal chelating agent; JP-A 15266/88 proposes a method for incorporating a radical chain inhibitor; JP-A 275661/89 proposes a method for incorporating a phosphinate- or phosphonate-containing amine compound or a salt thereof; JP-A 29257/89 proposes a method for incorporating a polyhydric metal oxide; JP-A 255804/90 and 179008/91 propose a method for performing polymerization in the presence of a water-soluble chain transfer agent, etc. Materials and methods described in JP-A 306202/96, 53884/95, 62252/95, 113048/95, 145326/95, 145263/95, 228788/95 and 228790/95 are also suitable. Specific examples include, for example, potassium titanate oxalate, tannic acid, titanium oxide, amine phosphinates (or salts thereof), amine phosphonates (or salts thereof), metal chelates, etc. Particularly, stabilizers against human urine, human blood and menstrual blood are sometimes called human urine stabilizers, human blood stabilizers and menstrual blood stabilizers, respectively.

Antibacterial agents are used to prevent spoiling by liquids absorbed. Suitable antibacterial agents can be appropriately selected from those introduced in, for example, "New development of bacteriocidal/antibacterial techniques", pp. 17–80 (Toray Research Center (1994)), "Test/evaluation methods and product designs of antibacterial/antifungal agents" pp. 128–344 (NTS (1997)), Japanese Patent No. 2760814, JP-A 179114/64, 31425/81, 25813/82, 189854/84, 105448/84, 155861/85, 181532/86, 135501/88, 139556/88, 156540/88, 5546/89, 5547/89, 153748/89, 221242/89, 253847/90, 59075/91, 103254/91, 321141/91, 11948/92, 92664/92, 138165/92, 266947/92, 9344/93, 68694/93, 161671/93, 179053/93, 269164/93, and 165981/95.

Suitable examples include, for example, alkyl pyridinium salts, benzalkonium chloride, chlorhexidine gluconate, zinc pyrithione, silver inorganic powders, etc. Typical examples of quaternary nitrogen antibacterial reagents include methylbenzethonium chloride, benzalkonium chloride, dodecyltrimethylammonium bromide, tetradecyltrimethylammonium bromide and hexadecyltrimethylammonium bromide. Heterocyclic quaternary nitrogen antibacterial reagents include dodecylpyridinium chloride, tetradecylpyridinium chloride, cetylpyridinium chloride (CPC), tetradecyl-4-ethylpyridinium chloride and tetradecyl-4-methylpyridinium chloride.

Other preferred antibacterial reagents are bis-biguanides, which are also known as antibacterial reagents. These are described in detail in U.S. Pat. Nos. 2,684,924, 2,990,425, 2,830,006 and 2,863,019, for example. The most preferred bisguanide is 1,6-bis(4-chlorophenyl) diguanide hexane, which is known as chlorhexidine and water-soluble salts thereof. Especially preferred are hydrochloride, acetate and gluconate of chlorhexidine.

Some other types of antibacterial reagents are also useful, such as carbanilides, substituted phenols, metal compounds and rare earth salts of surfactants. Carbanilides include 3,4,4'-trichlorcarbanilide (TCC, trichlocarban) and 3-(trifluoromethyl)-4,4'-dichlorcarbanilide (IRGASAN). Substituted phenols include 5-chloro-2-(2,4-dichlorophenoxy)phenol (IRGASAN DP-300). Metal compounds include salts of graphite and tin, such as zinc chloride, zinc sulfide and tin chloride. Rare earth salts of surfactants are disclosed in European Patent Publication No. 10819. This type of rare earth salts include lanthanum salts of straight C10–18 alkylbenzenesulfonates.

Deodorants, deodorizers and fragrances are used to prevent or reduce unpleasant odors of liquids absorbed. Suitable deodorants, deodorizers and fragrances can be appropriately selected from those introduced in, for example, "Technology and outlook for new deodorants/deodorizers" pp. 38–20 (Toray Research Center (1994)), JP-A 105448/84, 158861/85, 181532/86, 153748/89, 221242/89, 265956/89, 41155/90, 253847/90, 103254/91, 269164/93 and 277143/93. Specific examples of deodorants/deodorizers include iron complexes, tea-extracted components and activated carbon. Specific examples of fragrances include perfume-type pyroligneous acids (citral, cynnamic aldehyde, heliotropin, camphor, bornyl acetate), paradichlorobenzene, surfactants, higher alcohols, terpenic compounds (limonene, pinene, camphor, borneol, eucalyptol, eugenol).

Foaming agents and foaming aids can be used to increase pores/surface areas for the purpose of improving water-absorbing performance of water-absorbing resins. Suitable foaming agents and foaming aids can be appropriately selected from those introduced in, for example, "Additives for rubber/plastics" (Rubber Digest Co., 1989, pp. 259–267). Specific examples include sodium bicarbonate, nitroso compounds, azo compounds, sulfonyl hydrazides, etc.

These additives are appropriately added depending on the intended purpose and action mechanism during various steps of preparation processes of water-absorbing resins, water-absorbing composites and water-absorbing articles. For example, foaming agents are suitably added before or during polymerization in the preparation of water-absorbing resins.

Human urine stabilizers, human blood stabilizers, antibacterial agents, deodorants and fragrances can be added during various steps of preparation processes of water-absorbing resins, water-absorbing composites and water-absorbing articles. Naturally, they may also be preliminarily added to the fibrous substrate.

The present invention will now be further described by reference to certain Examples which are provided solely for purposes of limitation and are not intended to be limitative.

EXAMPLES

Example 1

To 125 parts by weight of an aqueous 80% by weight acrylic acid solution were added 57.3 parts by weight of an aqueous 48.5% by weight sodium hydroxide solution, 6.4 parts by weight of water, 0.15 parts by weight of a crosslinker (N,N'-methylenebisacrylamide) and 5.0 parts by weight of an aqueous 30% by weight hydrogen peroxide solution as an oxidizing agent to prepare solution A having a monomer concentration of 60% by weight and a neutrality of 50 mol %.

Separately, 57.3 parts by weight of an aqueous 48.5% by weight sodium, hydroxide solution, 9.9 parts by weight of water, 0.15 parts by weight of a crosslinker (N,N'-methylenebisacrylamide) and 1.5 parts by weight of L-ascorbic acid as a reducing agent was added to 125 parts by weight of an aqueous 80% by weight acrylic acid solution to prepare solution B having the same monomer concentration and neutrality as those of solution A.

The prepared solutions A and B were mixed with nozzles shown in FIG. 1, having an inner diameter of 0.13 mm and consisting of 5 nozzles for each solution spaced at intervals of 1 cm. The crossing angle between solutions A and B discharged from nozzles was 30° and the distance between nozzle tips of both solutions was 4 mm. Solutions A and B were warmed to 40° C. and pumped at a flow rate of 5 m/sec.

Solutions A and B were combined at the exit of the respective nozzle pairs to form liquid columns of about 10 mm and then divided into droplets to fall in a gas phase (in the air at a temperature of 50° C.) under polymerization. Some droplets collided with each other in the gas phase to form agglomerates, which fell on a polyester nonwoven fabric substrate (basic weight: 30 g/m$^2$) placed 3 m below the nozzles tips to complete polymerization on the substrate. In parallel, some droplets fell on said substrate to form agglomerates on the substrate, and then complete polymerization on said substrate. Thus, a water-absorbing polymer was supported on said substrate. The assembly was dried to a moisture content of 5% in the supported polymer to give water-absorbing composite A having a supported polymer level of 200 g/m$^2$.

Figure 2:
FIGS. 2 and 3 are light microphotographs of water-absorbing composite A prepared in Example 1.
Figure 3:
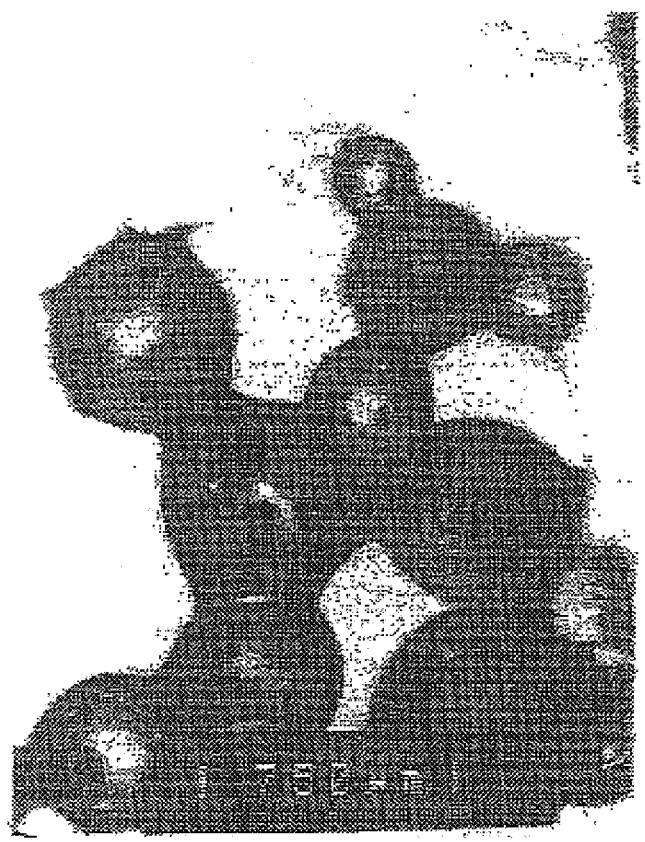
Figure 4:
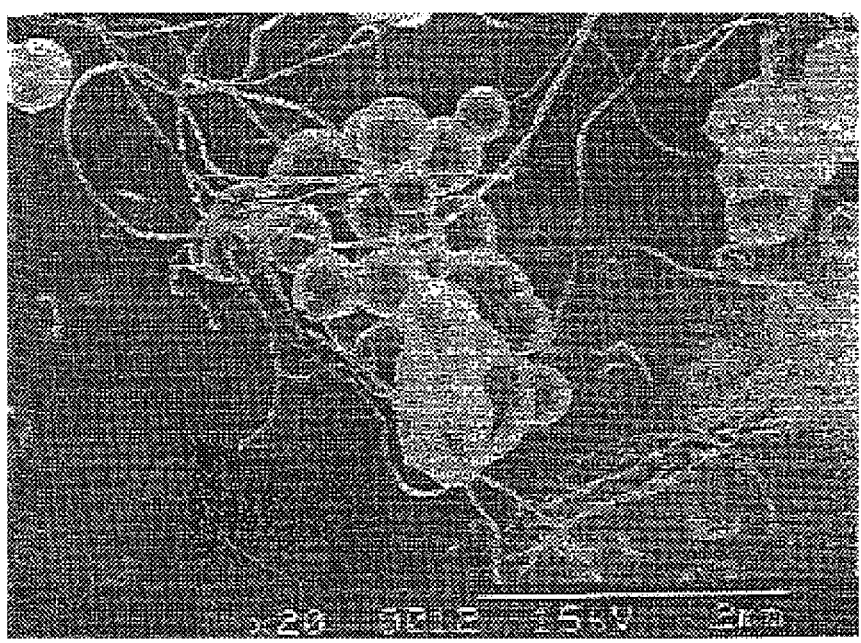
FIG. 4 is a scanning electron microphotograph of water-absorbing composite A prepared in Example 1.

Light microphotographs of this water-absorbing composite A are shown in FIGS. 2 and 3, and a scanning electron microphotograph of this water-absorbing composite A shown in FIG. 4.

Example 2

The procedure of Example 1 was repeated except that solution A used in Example 1 was replaced by a solution prepared by adding 80.4 parts by weight of 48.5% by weight potassium hydroxide, 2.0 parts by weight of water, 0.15 parts by weight of a crosslinker (N,N'-methylenebisacrylamide) and 5.0 parts by weight of an aqueous 30% by weight hydrogen peroxide solution as an oxidizing agent to 125 parts by weight of an aqueous 80% by weight acrylic acid solution and solution B used in Example 1 was replaced by a solution prepared by adding 80.4 parts by weight of 48.5% by weight potassium hydroxide, 5.5 parts by weight of water, 0.15 parts by weight of a crosslinker (N,N'-methylenebisacrylamide) and 1.5 parts by weight of L-ascorbic acid as a reducing agent to 125 parts by weight of an aqueous 80% by weight acrylic acid solution to give water-absorbing composite B.

Example 3

The procedure of Example 1 was repeated except that the polyester nonwoven fabric substrate used in Example 1 was replaced by a polypropylene/polyethylene nonwoven fabric substrate (basic weight: 100 g/m$^2$) to give water-absorbing composite C.

Example 4

The procedure of Example 1 was repeated except that the polyester nonwoven fabric substrate used in Example 1 was replaced by a rayon nonwoven fabric substrate (basic weight: 50 g/m$^2$) to give water-absorbing composite D.

Example 5

Undried water-absorbing composite A obtained in Example 1 (moisture content in the polymer 20%) was irradiated with UV-rays at 1000 mJ/cm$^2$ and then dried to a moisture content of 5% in the supported polymer to give water-absorbing composite E.

Example 6

The procedure of Example 1 was repeated except that the inner diameter of nozzles for solutions A and B used in Example 1 was changed to 0.20 mm to give water-absorbing composite F.

Example 7

The procedure of Example 1 was repeated except that solution A used in Example 1 was replaced by a solution prepared by adding 27.4 parts by weight of maleic anhydride, 68.9 parts by weight of 48.5% by weight sodium hydroxide, 18.0 parts by weight of water, 0.15 parts by weight of a crosslinker (N,N'-methylenebisacrylamide) and 5.0 parts by weight of an aqueous 30% by weight hydrogen peroxide solution as an oxidizing agent to 100 parts by weight of an aqueous 80% by weight acrylic acid solution and solution B used in Example 1 was replaced by a solution prepared by adding 27.4 parts by weight of maleic anhydride, 68.9 parts by weight of 48.5% by weight sodium hydroxide, 21.5 parts by weight of water, 0.15 parts by weight of a crosslinker (N,N'-methylenebisacrylamide) and 1.5 parts by weight of L-ascorbic acid as a reducing agent to 100 parts by weight of an aqueous 80% by weight acrylic acid solution to give water-absorbing composite G.

Example 8

An aqueous 5% ethylene glycol diglycidyl ether solution was sprayed with spray nozzles on water-absorbing composite A obtained in Example 1 to impregnate the polymer with the solution, and then the polymer was dried to a moisture content of 5% in the polymer to give water-absorbing composite H.

Example 9

The procedure of Example 1 was repeated except that the supported polymer content in Example 1 was changed to 100 g/m$^2$ to give water-absorbing composite I.

Comparative Example 1

Solutions A and B prepared in Example 1 were warmed to 40° C. and pumped at a flow rate of 5 m/sec using nozzles having an inner diameter of 0.13 mm.

Solution A formed liquid columns from nozzle tips and then became droplets to fall in a gas phase (in the air at a temperature of 50° C.). These droplets were received on a polyester nonwoven fabric substrate (basic weight: 30 g/m$^2$) placed 3 m below nozzles tips, and solution B prepared in Example 1 was sprayed in the same manner as for solution A.

Solutions A and B reacted with each other to advance polymerization, thus forming a water-absorbing polymer. This was dried to a moisture content of 5% to give water-absorbing composite J having a supported polymer content of 200 g/m$^2$.

Figure 5:
FIG. 5 is a light microphotograph of water-absorbing composite J prepared in Comparative example 1.

A light microphotograph of this water-absorbing composite J is shown in FIG. 5 using a scale of 1.5 mm.

Comparative Example 2

The procedure of Example 1 was repeated except that the polyester nonwoven fabric substrate used in Example 1 was placed 20 cm below nozzle tips, with the result that polymerization proceeded on the substrate to give water-absorbing composite L without forming agglomerates.

Comparative Example 3

The procedure of Example 1 was repeated except that the polyester nonwoven fabric substrate used in Example 1 was placed 5 m below nozzle tips to give water-absorbing composite M comprising almost completely polymerized agglomerates deposited on the substrate.

Comparative Example 4

Water-absorbing composite N was obtained by the process described in Example 1 of JP-A 67403/97.

Figure 6:
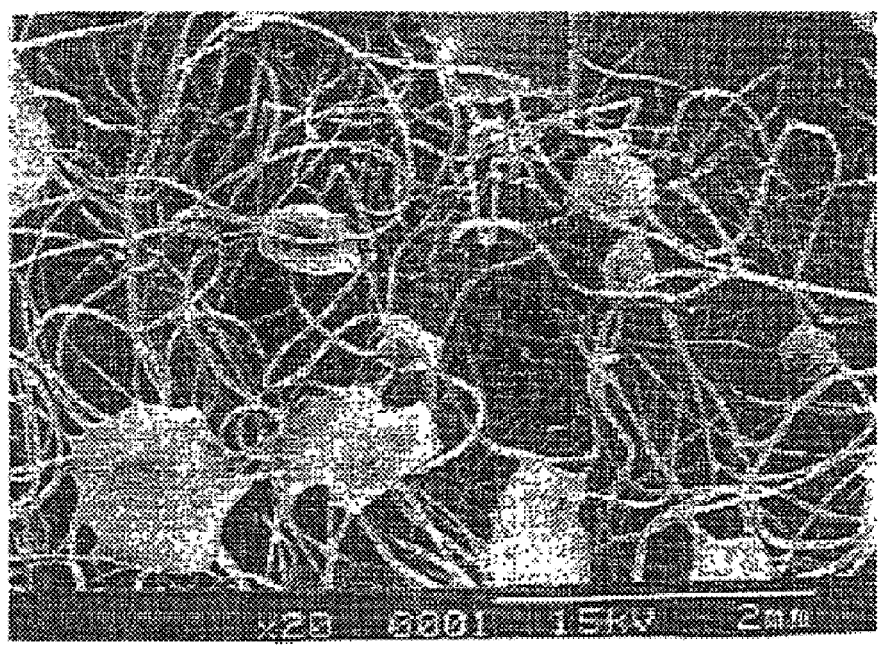
FIG. 6 is a scanning electron microphotograph of water-absorbing composite N prepared in Comparative example 4.
Figure 7:
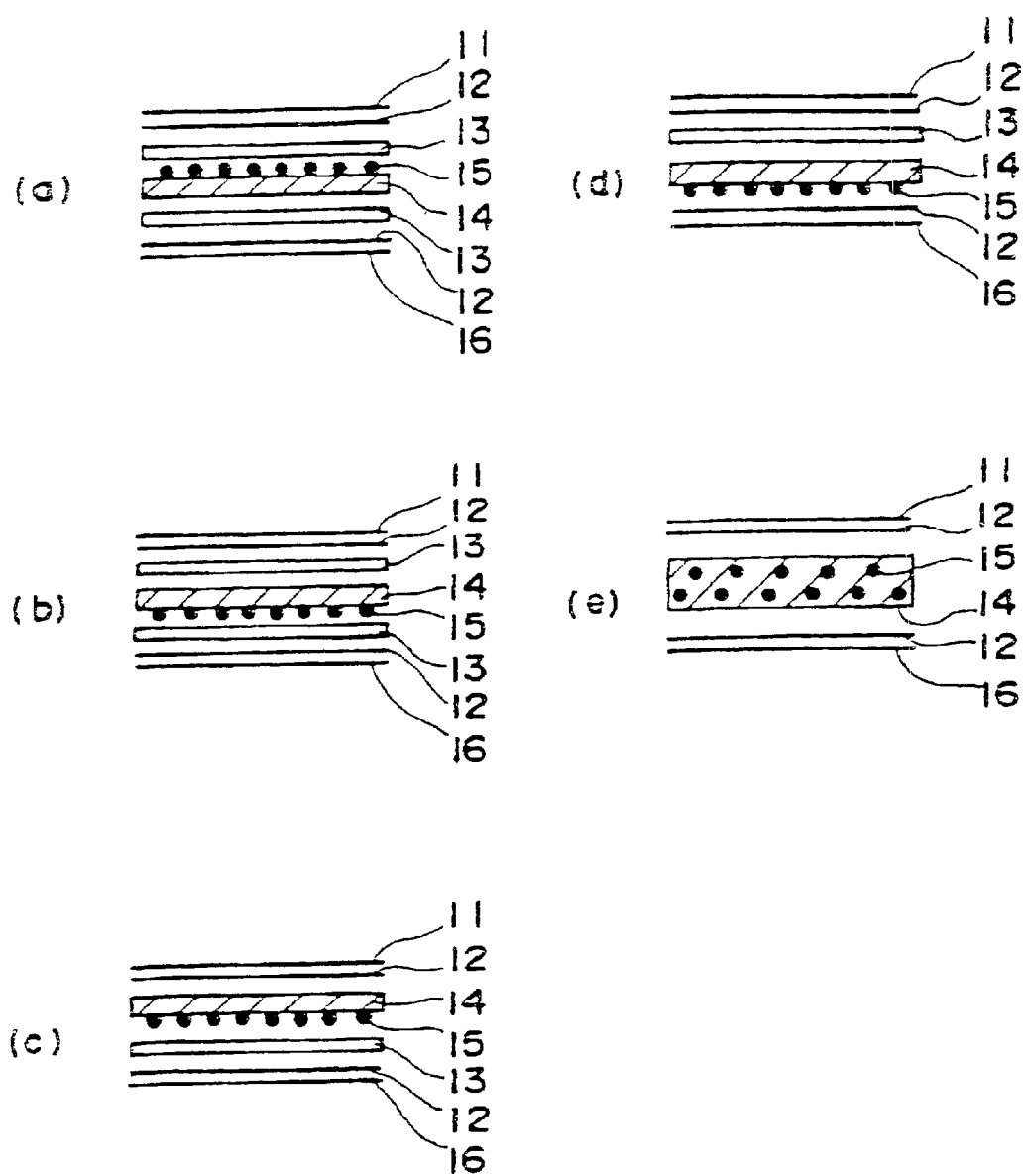
FIG. 7 is a sectional view showing the structure of the water-absorbing article prepared in Example 10, in which numeral references represent the following elements. 11: nonwoven cloth, 12: paper, 13: fluffy pulp, 14: fibrous substrate, 15: water-absorbing polymer particles, 16: polyethylene film.

A scanning electron microphotograph of this water-absorbing composite N is shown in FIG. 6 using a scale of 500 μm.

Comparative Example 5

Water-absorbing composite P was obtained by the process described in Example 1 of JP-A 239912/97.

Test Examples

Each water-absorbing composite obtained in Examples 1–9 and Comparative examples 1–5 was measured and tested as follows.

(1) Proportion of the Polymer in the Form of Agglomerates

On scanning electron microphotographs (SEM photographs) of plural sites of each water-absorbing composite, 100 particles were randomly selected to determine whether or not they form agglomerates. The proportion of the polymer in the form of agglomerates was calculated supposing that the density of agglomerates is homogeneous.

(2) Average Particle Diameter of Agglomerates

On SEM photographs of plural sites of each water-absorbing composite, 100 particles were randomly selected to measure their particle diameters, from which the average was calculated.

(3) Residual Unreacted Polymerizable Monomer Level

Precisely weighed 0.5 g of each water-absorbing composite was sufficiently swollen with 1 liter of ion-exchanged water in a 2-liter beaker with stirring for about 10 hours. The swollen polymer gel was filtered off through a 200-mesh sieve and the filtrate was analyzed by high-speed liquid chromatography. Separately, a monomer standard solution showing a known concentration was prepared to derive a calibration curve representing an absolute concentration scale.

(4) Supporting Strength of Water-absorbing Polymer to Fibrous Substrate

A sheet-like sample of 60 mm×300 mm (thickness: 0.5–20 mm) of each water-absorbing composite was absorbed with physiological saline to saturation and then placed on a stone table, and a roller having a diameter of 105 mm, a width of 60 mm and a weight of 4 kg was run on the sample to measure the dried weight of the water-absorbing polymer separated from the sample during 5 reciprocations at a speed of 10 cm/sec and to evaluate supporting percentage A represented by the equation below. The supporting percentage is preferably 60% or more for providing practically acceptable supporting strength, and more preferably 70% or more.

$$A(\%)=[(W0-w)/W0]\times 100$$

where W0 represents the dried weight of the water-absorbing polymer in the sample and w represents the dried weight of the separated water-absorbing polymer.

(5) Physiological Saline-absorbing Capacity

In a 300 ml beaker were weighed about 1.0 g of each water-absorbing composite and about 200 g of 0.9% physiological saline and allowed to stand for about 4 hours to sufficiently swell the polymer with physiological saline. After drainage through a 100-mesh sieve, physiological saline-absorbing capacity B was calculated according to the equation below to evaluate water-absorbing capacity of the supported water-absorbing polymer.

$$B=(W1-W2)/W3$$

where W1 represents the weight of the water-absorbing composite after absorbing water, W2 represents the weight of the substrate alone after absorbing water, and W3 represents the weight of the water-absorbing polymer supported on the water-absorbing composite.

(6) Water-absorbing Speed

In a 300 ml beaker were weighed about 1.0 g of each water-absorbing composite and about 200 g of 0.9% physiological saline and allowed to stand for 5 minutes to sufficiently swell the polymer with physiological saline. After drainage through a 100-mesh sieve, physiological saline-absorbing capacity B was calculated according to the equation above to evaluate water-absorbing speed of the supported water-absorbing polymer.

(7) Polymerization Degree During Falling on the Substrate

Polymerization was initiated to form droplets of the reaction mixture in a gas phase and the resulting agglomerates under polymerization were fallen in a beaker containing methanol weighed to have a liquid level in flush with the substrate. The monomer weight in methanol was determined by liquid chromatography. The polymer in methanol was dried under reduced pressure at 130° C. for 3 hours, and then the weight was determined. The polymerization degree was calculated from both weights according to the equation below.

$$\text{Polymerization degree}=Mp/(Mm+Mp)\times 100$$

where Mp represents the polymer weight and Mm represents the monomer weight.

(8) Frequency Intensity Ratio

Agglomerates were photographed at a magnification of 160× or 300× using a scanning electron microscope (Hitachi S2400). Particle contours on these photographs were faithfully traced with a mechanical pencil (HB, 0.5 mm φ) on a tracing paper and the traced image was reduced to a half for image analysis. The image was scanned with a scanner (Canon CanoScan 300) at a resolution of 75 dpi. The resolution of measurable length in the scanned image was 2.3 μm (80×) or 1.25 μm (150×). The scanned contour image was converted into text file after the inside of the contour image was painted out (using a commercially available software such as Adobe Photoshop and NIH image, for example).

The painted figure including the contour was expressed as a binary pattern (0,1) to find the center of gravity (Gx, Gy). If all the four pixels on four sides surrounding a target black pixel are "1", the target pixel was judged as an inner pixel to determine the contour (a closed curve of the boundary of the figure). Then, black pixels forming the contour were continuously traced to derive the coordinate sequence (Xi, Yi) of the contour line consisting of m data.

The distances between the center of gravity and pixels forming the contour line were determined for the whole coordinate sequence of the contour line, and then the distances from the center of gravity were normalized by dividing each distance from the center of gravity by the average distance and subtracting "1" to give a normalized distance.

Normalized distance=(Distance from center of gravity/average distance)−1

Before frequency analysis of the normalized distances, the number of data varying with particles was normalized to 512. In order to convert m data of normalized distances into 512 data, 2 data flanking a target datum were used for interpolation.

The normalized distance consisting of a sequence of 512 data was Fourier-transformed to derive a power spectrum. The power spectrum was integrated from low to high frequency sides to give the integral of the power spectrum.

To define features of the figure, the ratio between the integral at frequency 5 (Ipw, 5) and the integral at frequency 20 (Ipw, 20) of the power spectrum was determined as frequency intensity ratio. The frequency intensity ratio is greater for ellipses or similar figures (containing much low-frequency components), but smaller for figures with complex contour lines (containing much high-frequency components).

Frequency intensity ratio=$(Ipw, 5)/(Ipw, 20)$.

(9) Average Relative Displacement of the Direction

A relative displacement of the direction ($\Delta\theta$) was calculated from the coordinate sequence (Xi, Yi) of the contour line. The relative displacement of the direction is defined by the equation below. That is, the relative displacement of the direction of an i-th contour datum ($\Delta\theta$) is a directional difference between a vector joining the i-th datum (Xi, Yi) to a (i+n)-th datum (Xi+n, Yi+n) and a vector joining a (i+n)-th datum (Xi−n, Yi−n) to the i-th datum (Xi, Yi) and the relative displacement of the direction is 0° degree, if both vectors have the same direction. There is no discrimination between right and left directions of variation.

$$\Delta\theta i=(\tan^{-1}(Yi+n-Yi)/(Xi+n-Xi)-\tan^{-1}(Yi-Yi-n)/(Xi-Xi-n))\times 180/\pi$$

where n=5 in view of the minimum variation angle of 45° (π/4 radian), which causes too large stepping pitch to increase the influence of digitization error if n=1. The relative displacement of the direction was calculated according to the equation below.

Average relative displacement of the direction ($\theta$)=($\Delta\theta i$−360×n)/number of data (m)

where the correction term "360xn" was introduced because the sum of relative displacement of the direction is 360° even for a circle n was introduced because the sum of all the data means the sum of n relative displacement direction.

The average relative displacement of the direction is a value defining complexity of a particle contour line and it is greater for complex shapes having a more irregular contour.

Calculations were made considering that coordinate sequences (X1, Y1) and (Xm, Ym) are continuous because coordinate data in these data processes are characterized by a closed curve of a contour line. The average of randomly sampled three or more particles was used for digitization.

(10) The Maximum Length/Minimum Length Ratio

The Maximum and minimum length of agglomerates were determined from processed processed images of agglomerates. As used herein, the maximum and minimum length refer to the maximum and minimum lengths as diameters of agglomerates but may not be necessarily orthogonal. The maximum length/minimum length ratio was calculated by dividing the maximum length by the minimum length. Any material having a maximum length/minimum length ratio less than 1.2 cannot be considered as an agglomerate structure.

These measurements and test results are summarized in the table below.

TABLE 1

| Example/Comparative example | Examples | | | | | | | | | Comparative Examples | | | | |
|---|---|---|---|---|---|---|---|---|---|---|---|---|---|---|
| | 1 | 2 | 3 | 4 | 5 | 6 | 7 | 8 | 9 | 1 | 2 | 3 | 4 | 5 |
| Water-absorbing composite | A | B | C | D | E | F | G | H | I | J | L | M | N | P |
| Proportion of the polymer in the form of agglomerates (%) | 85 | 80 | 85 | 83 | 86 | 79 | 75 | 86 | 72 | 3 | 8 | 68 | 0 | 95 |

TABLE 1-continued

| Example/Comparative example | Examples | | | | | | | | | Comparative Examples | | | | |
|---|---|---|---|---|---|---|---|---|---|---|---|---|---|---|
| | 1 | 2 | 3 | 4 | 5 | 6 | 7 | 8 | 9 | 1 | 2 | 3 | 4 | 5 |
| Average particle diameter of agglomerates ($\mu$m) | 550 | 600 | 500 | 520 | 530 | 750 | 460 | 550 | 460 | little grains | little grains | 450 | 200 | 500 |
| Physiological saline-absorbing capacity (g/g) | 40 | 35 | 37 | 41 | 38 | 34 | 30 | 37 | 43 | 20 | 22 | 44 | 35 | 35 |
| Water-absorbing speed (g/g) | 30 | 27 | 36 | 29 | 32 | 25 | 20 | 32 | 34 | 10 | 11 | 35 | 23 | 25 |
| Residual unreacted polymerizable monomer level (ppm) | 150 | 170 | 140 | 160 | 60 | 180 | 190 | 130 | 180 | 2000 | 350 | 90 | 200 | 200 |
| Supporting strength of water-absorbing polymer to fibrous substrate (%) | 80 | 78 | 75 | 83 | 83 | 82 | 74 | 82 | 84 | 92 | 87 | 15 | 85 | 94 |
| Polymerization degree during falling on the substrate (%) | 82 | 90 | 82 | 82 | 82 | 75 | 60 | 82 | 82 | 0 | 0 | 99 | 15 | — |
| Frequency intensity ratio | 0.75 | 0.69 | 0.73 | 0.74 | 0.73 | 0.62 | 0.8 | 0.74 | 0.77 | 0.7 | 0.68 | 0.88 | 0.74 | 0.58 |
| Average relative displacement of the direction by direction analysis | 18 | 14 | 19 | 20 | 18 | 21 | 13 | 21 | 16 | 4 | 6 | 9 | 8 | 11 |
| Aspect ratio | 1.8 | 1.8 | 1.3 | 1.8 | 1.7 | 1.5 | 1.3 | 1.6 | 1.3 | 1.1 | 1.1 | 1.2 | 1.2 | 1.3 |

Example 10

Solution A was prepared by adding 9 parts by weight of an aqueous 30% by weight hydrogen peroxide solution to 237.4 parts by weight of a partially neutralized aqueous acrylic acid solution (monomer content 50% by weight) containing N,N'-methylenebisacrylamide at 0.07 mol % on the basis of (preneutralized) acrylic acid in acrylic acid neutralized to 60% with sodium hydroxide. Solution B was prepared by adding 1.0 part by weight of L-ascorbic acid to 237.4 parts by weight of the same aqueous acrylic acid solution. The prepared solutions A and B were flown out at a rate of 5 m/sec from their respective nozzles (inner diameter 0.1 mm) provided at the ceiling of a polymerization chamber containing a polyester nonwoven cloth (fiber diameter 25–30 $\mu$m, basic weight 35 g/m$^2$) on the floor level and opposed to each other at a height of 3 m above the floor level. Both solutions were collided in the air to form droplets, which were fallen on the nonwoven cloth forming a fibrous substrate as they were polymerized in an atmosphere at 40–50° C. Then, the nonwoven cloth on which incompletely polymerized particles were deposited was removed from the polymerization chamber and heated to complete polymerization into water-absorbing composite Q. The resulting water-absorbing composite Q had a water-absorbing polymer particle content of 200 g/m$^2$. Polymer particles had a primary particle diameter of 100–600 $\mu$m and agglomerates of primary particles had a particle diameter of 300–3000 $\mu$m. The proportion of agglomerates was about 90% or more.

Thus prepared water-absorbing composite Q and water-absorbing composite N prepared in Comparative example 4 were used as absorbent materials to prepare 6 types of water-absorbing articles (diapers) having a structure as defined in Table 2 selected from FIGS. 7(a)–(e). The articles were prepared to have a water-absorbing face at the top on the figure. Each structure contains a polyethylene film 16 (basic weight 20 g/m$^2$), a fluffy pulp layer 13 (basic weight 110.5 g/m$^2$), a water-absorbing material having water-absorbing polymer particles 15 immobilized on a fibrous substrate 14, a tissue paper 12 (basic weight 18 g/m$^2$) and a polyester fiber nonwoven cloth 11 (basic weight 30 g/m$^2$). However, the structure of FIG. 7(e) uses a pulp mix having water-absorbing polymer particles uniformly dispersed in fluffy pulp in place of the water-absorbing material having water-absorbing polymer particles bonded to one side of a fibrous substrate. The pulp mix was prepared by combining water-absorbing polymer particles obtained as above but not adhered to the nonwoven cloth and said fluffy pulp at a water-absorbing polymer content of 200 g/m$^2$ and a pulp content of 256 g/m$^2$.

Each diaper prepared was tested for the speed of absorbing artificial urine and the amount of artificial urine released as follows. An acrylic plate (100×100×10 mm, overall weight 150 g) equipped at the center with a cylinder of 40 mm in inner diameter opened at the top and having 7 penetrations of 5 mm in diameter almost evenly spaced inside the circle surrounded by the cylinder was mounted at the center of each diaper prepared (180×180 mm), and a disk (500 g) of 100 mm in diameter having a hole of 45 mm in diameter at the center was further mounted through the cylinder. Artificial urine (25 ml) was introduced into the cylinder to measure the time with a stopwatch until it is absorbed. After 10 minutes, the disk and acrylic plate were removed and 20 plies of filter paper (ADVANTEC No. 424, 100×100 mm, Toyo Roshi) were mounted at the same position as that of the acrylic plate on the diaper and a weight of 4 kg was further mounted on the filter paper. After 5 minutes, the weight was removed and the weight of the filter paper was measured to determine the amount of artificial urine absorbed to the filter paper. This measurement was repeated three times. The results are shown in the table below, in which the water-absorbing speed is expressed in seconds and the released amount is expressed in g.

agglomerates stably immobilized on a fibrous substrate. They exhibit excellent water-absorbing properties, a high water-absorbing speed and an excellent immobility of swollen gel after absorbing water. According to processes of the present invention, water-absorbing composites exhibiting excellent performance can be simply and economically prepared with little residual monomer content. Therefore, water-absorbing articles using a water-absorbing composite of the present invention or a water-absorbing composite prepared by a process of the present invention are of very high practical value and utility.

Having described the present invention, it will now be apparent to one of ordinary skill in the art that many changes and modifications may be made without departing from the spirit and the scope of the present invention.

TABLE 2

| | | | First test | | Second test | | Third test | | Total | |
| --- | --- | --- | --- | --- | --- | --- | --- | --- | --- | --- |
| Sample | Water-absorbing composite | Structure | Water-absorbing speed | Released amount | Water-absorbing speed | Released amount | Water-absorbing speed | Released amount | Water-absorbing speed | Released amount |
| 1 | Q | a | 5.7 | 2.0 | 80.0 | 4.5 | 122.6 | 6.9 | 208.3 | 13.4 |
| 2 | Q | b | 4.8 | 5.0 | 12.2 | 5.0 | 22.9 | 6.0 | 39.9 | 16.0 |
| 3 | Q | c | 4.2 | 1.9 | 7.1 | 1.9 | 8.8 | 4.1 | 20.1 | 7.9 |
| 4 | Q | d | 5.3 | 10.3 | 11.8 | 9.8 | 18.5 | 10.7 | 35.6 | 30.8 |
| 5 | Q | e | 6.0 | 0.2 | 38.1 | 4.8 | 56.0 | 12.7 | 100.1 | 17.7 |
| 6 | N | c | 4.9 | 1.2 | 10.3 | 4.9 | 14.0 | 7.1 | 29.2 | 13.2 |

When comparing the results of samples 1 and 2, the diaper of sample 1 having a water-absorbing face on the water-absorbing resin particle side shows much lower water-absorbing speeds in the second and third tests as compared with the diaper of sample 2 having a water-absorbing face on the fibrous substrate side according to the present invention. Among diapers of the present invention, sample 3 having a fluffy pulp layer on the water-absorbing resin particle side is superior to sample 4 having a fluffy pulp layer on the fibrous substrate side in both absorbing speed and released amount. Sample 5 is a conventional diaper, which shows lower water-absorbing speeds in the second and third tests.

The diapers of sample 2 and sample 5 prepared as above were tested for the transfer amount of water-absorbing resin particles in the diapers when a force rubbing the diapers was repeatedly applied. Each diaper of 180×180 mm having absorbed water in an amount 50 times the weight of the water-absorbing resin was mounted on a shaking table, and an acrylic plate of 120×120 mm curved in a semicircle was further mounted thereon so that the outer center of the semicircle coincides with the center of the diaper. The inner center of the semicircle has an insertion part, in which the post of a T-shaped weight (3 kg) was loosely inserted while it was supported at the center of a plate of 100×100 mm. When the shaking table oscillates, the weight swings around the post so that the acrylic plate reciprocates to rub the diaper. After the shaking table was oscillated for 5 minutes at 80 reciprocations/min, the center of the diaper was cut out into a size of 100×100 mm to determine the reduction percentage of water-absorbing resin particles. The results showed that the reduction percentage of the water-absorbing resin of the diaper of sample 2 was 15% in contrast to the diaper of sample 5 in which the reduction was 29%, i.e. almost doubled.

In water-absorbing composites of the present invention, most of the highly water-absorbing polymer forms proper

What is claimed is:

1. A water-absorbing composite, comprising:
    water-absorbing polymer particles immobilized on a fibrous substrate;
    wherein at least a part of said water-absorbing polymer particles comprise primary particles having an average particle diameter of about 50–1000 $\mu$m;
    wherein about 30% by weight or more of said primary particles are combined to form agglomerates having a shape satisfying the following conditions while nearly maintaining their primary particle shapes and a part of particles of said agglomerates are not adhered to said fibrous substrate:
    Average particle diameter (D) $100 \leq D \leq 3000$ $\mu$m
    Average relative displacement of the direction by direction analysis ($\theta$) $10 \leq \theta \leq 25$
    Frequency analysis 5 Hz/20 Hz intensity ratio (k) $0.6 \leq k \leq 0.9$
    Agglomerate maximum length (L)/minimum length (l) ratio $1.2 \leq L/l \leq 15.0$;
    wherein said water-absorbing composite is produced by
        forming droplets of a reaction mixture obtained by mixing a) an aqueous solution of a polymerizable monomer giving a water-absorbing polymer with b) a redox polymerization initiator in a gas phase,
        combining said droplets into agglomerates while nearly maintaining their primary particle shapes in the gas phase and/or on a fibrous substrate,
        supporting said agglomerates formed in the gas phase on said fibrous substrate, and
        then completing polymerization of said agglomerates on said fibrous substrate to immobilize said agglomerates on said fibrous substrate.

2. The water-absorbing composite of claim 1, wherein about 50% by weight or more of said water-absorbing polymer particles form said agglomerates.

3. The water-absorbing composite of claim 1, wherein about 80% by weight or more of said water-absorbing polymer particles form said agglomerates.

4. The water-absorbing composite of claim 1, wherein said fibrous substrate comprises synthetic fibers, natural fibers, or semisynthetic fibers or a combination thereof.

5. The water-absorbing composite of claim 1, wherein the fibrous substrate comprises hydrophilic fibers.

6. The water-absorbing composite of claim 5, wherein the hydrophilic fibers comprise wood pulp, rayon, cotton or cellulose fibers.

7. The water-absorbing composite of claim 4, wherein the fibrous substrate comprises fibers of polyester, polyethylene, polypropylene, polystyrene, polyamide, polyvinyl alcohol, polyvinyl chloride, polyvinylidene chloride, polyacrylonitrile, polyurea, polymethane, polyfluoroethylene or polyvinylidene cyanide.

8. The water-absorbing composite of claim 4, wherein the fibrous substrate comprises paper, wood or leather.

9. The water-absorbing composite of claim 1, wherein said primary particles have an average particle diameter of about 100–900 μm.

10. The water-absorbing composite of claim 9, wherein said primary particles have an average particle diameter of about 200–800 μm.

11. The water-absorbing composite of claim 1, wherein said agglomerates have an average particle diameter of about 200–2,000 μm.

12. The water-absorbing composite of claim 11, wherein said agglomerates have an average particle diameter of about 250–2,000 μm.

13. The water-absorbing composite of claim 1, wherein said agglomerates exhibit an average relative displacement of the direction by direction analysis (θ) of from 12–24.

14. The water-absorbing composite of claim 13, wherein said agglomerates exhibit an average relative displacement of the direction by direction analysis (θ) of from 14–22.

15. The water-absorbing composite of claim 1, wherein said agglomerates exhibit a frequency analysis 5 Hz/20 Hz intensity ratio (k) of from 0.65–0.85.

16. The water-absorbing composite of claim 15, wherein said agglomerates exhibit a frequency analysis 5 Hz/20 Hz intensity ratio (k) of from 0.65–0.80.

17. The water-absorbing composite of claim 1, wherein said agglomerates have a ratio of maximum length (L)/minimum length (l) of from 1.5–10.0.

18. The water-absorbing composite of claim 17, wherein said agglomerates have a ratio of maximum length (L)/minimum length (l) of from 1.5–8.0.

19. The water-absorbing composite of claim 1, which comprises said water-absorbing polymer particles in an amount of from about 50–300 g/m$^2$.

20. The water-absorbing composite of claim 19, which comprises said water-absorbing polymer particles in an amount of from about 100–250 g/m$^2$.

21. The water-absorbing composite of claim 20, which comprises said water-absorbing polymer particles in an amount of from about 130–220 g/m$^2$.

22. The water-absorbing composite of claim 1, wherein said agglomerates are formed by polymerizing an aqueous ethylenically unsaturated monomer solution with a redox polymerization initiator.

23. A process for preparing a water-absorbing composite according to claim 1, comprising:
   a) forming droplets of a reaction mixture initiated by mixing i) an aqueous solution of a polymerizable monomer giving a water-absorbing polymer with a ii) redox polymerization initiator in a gas phase;
   b) combining said droplets into agglomerates while nearly maintaining their primary particle shapes in the gas phase or on a fibrous substrate, or both;
   c) supporting said agglomerates formed in the gas phase on said fibrous substrate; and then
   d) completing polymerization of said agglomerates on said fibrous substrate to immobilize said agglomerates thereon.

24. The process of claim 23, wherein said polymerizable monomer has a polymerization degree of about 20–97% when it comes into contact with said fibrous substrate.

25. The process of claim 23, wherein said droplets of a reaction mixture are formed by mixing a first solution containing an oxidizing agent forming the redox polymerization initiator and the aqueous polymerizable monomer solution and a second solution containing a reducing agent forming the redox polymerization initiator and the aqueous polymerizable monomer solution in a gas phase.

26. The process of claim 25, wherein said mixing is performed by colliding said first solution and said second solution in a liquid column state.

27. The process of claim 23, wherein said polymerizable monomer is based on an aliphatic unsaturated carboxylic acid or a salt thereof.

28. The process of claim 23, wherein said polymerizable monomer is based on acrylic acid in which 20 mol % or more of the carboxyl group is neutralized into an alkali metal salt or an ammonium salt.

29. The process of claim 23, wherein the oxidizing agent forming said redox polymerization initiator is hydrogen peroxide and the reducing agent is L-ascorbic acid or an L-ascorbic acid alkali metal salt.

30. The process of claim 23, wherein said fibrous substrate comprises synthetic fibers, natural fibers, or semisynthetic fibers.

31. A water-absorbing article, comprising:
   a water-absorbing material having water-absorbing polymer particles immobilized on one side of a fibrous substrate so that said water-absorbing polymer particles absorb aqueous liquids through said fibrous substrate,
   wherein immobilization of said water-absorbing polymer particles comprises
   a) forming droplets of a reaction mixture initialized by mixing i) an aqueous solution of a polymerizable monomer giving a water-absorbing polymer with ii) a redox polymerization initiator in a gas phase,
   b) combining said droplets into agglomerates while nearly maintaining their primary particle shapes in the gas phase or on a fibrous substrate or both,
   c) supporting said agglomerates formed in the gas phase on said fibrous substrate, and then
   d) completing polymerization of said agglomerates on said fibrous substrate to immobilize said agglomerates on said fibrous substrate.

32. The water-absorbing article of claim 31, wherein said fibrous substrate is in the form of a sheet.

33. The water-absorbing article of claim 32, wherein said fibrous substrate is a nonwoven cloth.

34. The water-absorbing article of claim 33, wherein said fibrous substrate is a nonwoven cloth consisting of fibers having a diameter of about 10–50 μm.

35. The water-absorbing article of claim 31, wherein said fibrous substrate has a basic weight of about 10–100 g/m$^2$.

36. The water-absorbing article of claim 31, wherein the surfaces of said water-absorbing polymer particles are crosslinked.

37. The water-absorbing article of claim 31, wherein said water-absorbing polymer particles are immobilized on said fibrous substrate at 50–300 g/m$^2$.

38. The water-absorbing article of claim 31, wherein a fluffy pulp layer is provided on the water-absorbing polymer particle side of said water-absorbing material.

39. The water-absorbing article of claim 38, wherein a fluffy pulp layer is provided on each side of said water-absorbing material and the fluffy pulp layer provided on the water-absorbing polymer particle side has a greater basic weight than that of the fluffy pulp layer provided on the fibrous substrate side.

40. The water-absorbing article of claim 38, wherein the fluffy pulp layer provided on the water-absorbing polymer particle side of said water-absorbing material has a basic weight of about 80–250 g/m$^2$.

41. The water-absorbing article of claim 31, wherein said fibrous substrate is in the form of a sheet.

42. The water-absorbing article of claim 41, wherein said fibrous substrate is a nonwoven cloth.

43. The water-absorbing article of claim 42, wherein said fibrous substrate is a nonwoven cloth consisting of fibers having a diameter of about 10–50 μm.

44. The water-absorbing article of claim 31, wherein said fibrous substrate has a basic weight of about 10–100 g/m$^2$.

45. The water-absorbing article of claim 31, wherein the surfaces of said water-absorbing polymer particles are crosslinked.

46. The water-absorbing article of claim 31, wherein said water-absorbing polymer particles are immobilized on said fibrous substrate at 50–300 g/m$^2$.

47. The water-absorbing article of claim 31, wherein a fluffy pulp layer is provided on the water-absorbing particle side of said water-absorbing material.

48. The water-absorbing article of claim 47, wherein a fluffy pulp layer is provided on each side of said water-absorbing material and the fluffy pulp layer provided on the water-absorbing polymer particle side has a greater basic weight than that of the fluffy pulp layer provided on the fibrous substrate side.

49. The water-absorbing article of claim 47, wherein the fluffy pulp layer provided on the water-absorbing polymer particle side of said water-absorbing material has a weight of about 80–250 g/m$^2$.

* * * * *

UNITED STATES PATENT AND TRADEMARK OFFICE
CERTIFICATE OF CORRECTION

PATENT NO. : 6,797,656 B2
DATED : September 28, 2004
INVENTOR(S) : Hiroyoshi Tsuchiya et al.

It is certified that error appears in the above-identified patent and that said Letters Patent is hereby corrected as shown below:

Title page,
Item [63], Related U.S. Application Data, should read;
-- Related U.S. Application Data
(63) Continuation of application No. PCT/JP99/06176, filed on Nov. 5, 1999. --

Signed and Sealed this

Fourteenth Day of December, 2004

JON W. DUDAS
*Director of the United States Patent and Trademark Office*